United States Patent [19]

Green et al.

[11] Patent Number: 4,881,544
[45] Date of Patent: Nov. 21, 1989

[54] SURGICAL STAPLER APPARATUS WITH IMPROVED TISSUE SHIELD

[75] Inventors: David T. Green, Westport; Ernest Aranyi, Easton, both of Conn.

[73] Assignee: United States Surgical Corporation, Norwalk, Conn.

[21] Appl. No.: 286,507

[22] Filed: Dec. 19, 1988

[51] Int. Cl.⁴ .......................... A61B 17/04; B31B 1/00
[52] U.S. Cl. .................................. 227/178; 227/901; 227/19
[58] Field of Search ........ 128/334 R; 227/19, DIG. 1

[56] References Cited

U.S. PATENT DOCUMENTS 4,354,628  10/1982  Green .................................. 227/19
4,665,916  5/1987  Green ............................. 128/334 R Primary Examiner—Edward M. Coven
Assistant Examiner—Gary Jackson
Attorney, Agent, or Firm—Dilworth & Barrese

[57] ABSTRACT

An improved surgical stapler for simultaneously applying a plurality of surgical fasteners to body tissue, incorporating a flexible and resilient shield assembly comprising a substantially U-shaped wedge member mounted to and around the end of the anvil assembly, for separating extraneous body tissue from tissue to be fastened, and two shutter blades mounted on the sides of the wedge member for preventing extraneous body tissue from entering into the gap between the anvil assembly and fastener holder.

20 Claims, 5 Drawing Sheets

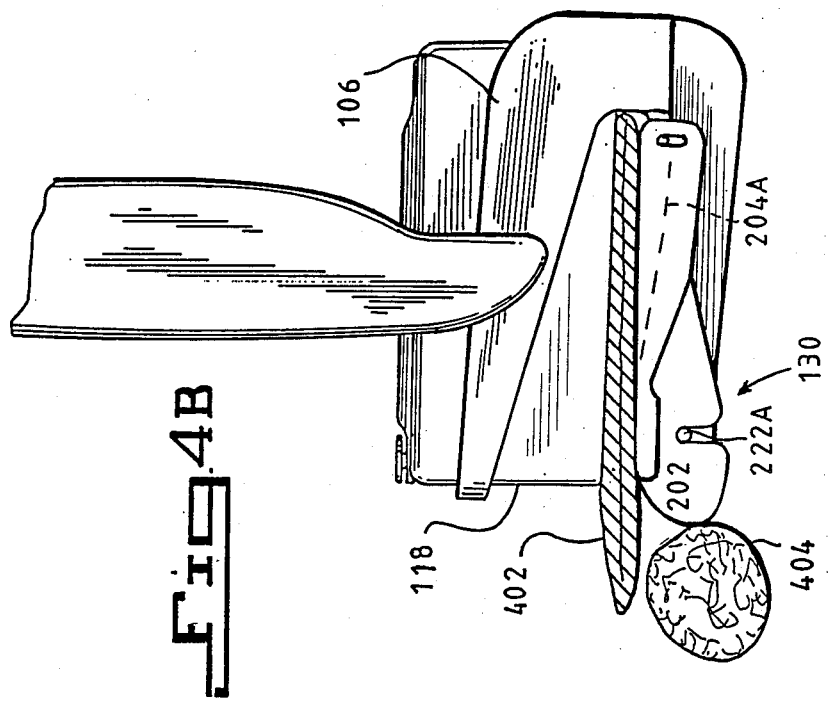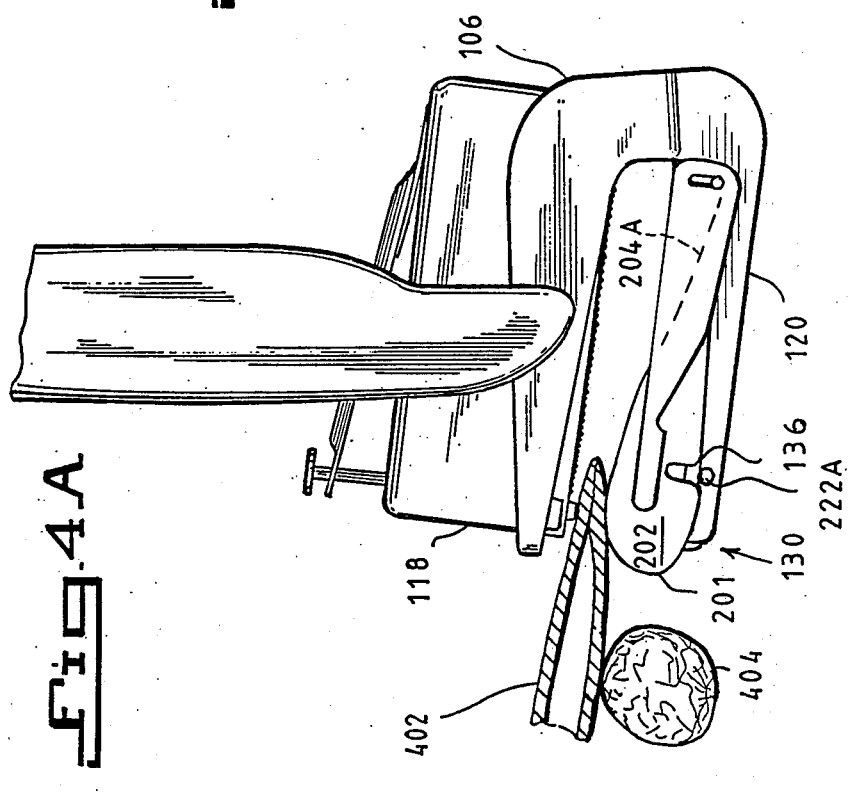

SURGICAL STAPLER APPARATUS WITH IMPROVED TISSUE SHIELD

BACKGROUND OF THE INVENTION

1. Field Of The Invention:

This invention relates to surgical stapling apparatus, and more particularly to a surgical stapling apparatus incorporating a safety shield for protecting extraneous body tissue from the operation of the stapler.

2. Description Of Related Art:

Surgical stapling apparatus in which a plurality of surgical fasteners are applied substantially simultaneously to produce an array of surgical fasteners are known. Typically these apparatus include a fastener holder disposed on one side of the tissue to be fastened, an anvil assembly parallel to the fastener holder on the other side of the tissue to be fastened, means for linearly translating the fastener holder and the anvil assembly toward one another so that the tissue is clamped between them, and means for driving the fasteners from the fastener holder so that the ends of the fasteners pass through the tissue and form finished fasteners as they make contact with the anvil assembly, thereby producing an array of finished fasteners in the tissue. The term "fasteners" is used herein as a generic term for metal surgical staples, the staple-shaped portion of one part or two part resinous surgical fasteners, and their equivalents. Similarly, the term "anvil assembly" is used herein as a generic term to include the anvil used to clinch metal surgical staples, the retainer holder and retainer member of two-part resinous surgical fasteners, and the equivalent of these elements.

In common use are devices such as those disclosed in U.S. Pat. Nos. 4,354,628 and 4,665,916. More particularly, U.S. Pat. No. 4,354,628 discloses a surgical stapler apparatus for forming an array of surgical staples in body tissue including an anvil member against which the staples are crimped, and a staple holder pivotally mounted adjacent one end of the anvil member.

U.S. Pat. No. 4,665,916 discloses a surgical stapling apparatus comprising an anvil assembly against which fasteners are formed and a fastener holder pivotally mounted adjacent one end of the anvil assembly, a spacer member at the other end so constructed to displace tissue that would otherwise obstruct the spacer member from properly positioning the fastener holder relative to the anvil assembly to insure proper fastener formation, and a knife assembly to cut the tissue between the rows of formed fasteners.

Surgeons use such devices by selecting, or targeting the body tissue to be fastened, positioning the stapler mechanism so that the target tissue is between the anvil assembly and the fastener holder, then actuating the fastener holder and drive mechanism. In some surgical applications, though, it is possible to have extraneous untargeted tissue enter the gap between the anvil assembly and the fastener holder when the surgeon is positioning the mechanism. If the extraneous tissue is covered by the target tissue the surgeon may inadvertently activate the stapler mechanism and damage the extraneous surrounding tissue. This problem may occur, for example, in caesarean section procedures when fetal tissue may inadvertently enter the stapler mechanism as the surgeon is carrying out the procedure.

Clearly, therefore, there is a need to provide a surgical stapler whereby the extraneous tissue is protected from the operation of the stapler.

SUMMARY OF THE INVENTION

Accordingly, it is one object of the present invention to provide a surgical stapling apparatus.

It is another object of the present invention to provide a surgical stapling apparatus to fasten body tissue.

It is another object of the present invention to provide a surgical stapling apparatus to simultaneously cut body tissue and apply a plurality of surgical fasteners to body tissue.

It is another object of the present invention to provide a surgical stapling apparatus which isolates the tissue to be joined.

It is yet another object of the present invention to provide a surgical stapling apparatus which shields surrounding tissue from the operation of the stapler.

These and other advantages are accomplished herein in an improved surgical stapler mechanism for substantially simultaneously applying a plurality of surgical fasteners to body tissue comprising a handle, a gripping lever, a frame with a U-shaped distal portion, an anvil assembly mounted at the distal leg of the U-shaped distal portion, a fastener holder pivotally connected to the anvil assembly adjacent one end of the anvil assembly thereby defining a gap between them and containing a plurality of surgical fasteners and optionally, including a knife means for cutting body tissue, the stapler mechanism further including a fastener driving means for substantially driving all of the fasteners from the fastener holder, and means for actuating the fastener holder, the improvement comprising:

shield assembly means mounted on the sides of the anvil assembly for preventing extraneous body tissue from being operated upon by the surgical stapler, said shield assembly means comprising a wedge member, for separating extraneous tissue from the body tissue to be fastened and two shutter blades acting in cooperation with the wedge member for deflecting extraneous tissue form entering the gap between the anvil assembly and the fastener holder.

Further features of the invention, its nature and various objects will be more apparent from the accompanying drawings and the following detailed description of the invention.

BRIEF DESCRIPTION OF THE DRAWINGS

FIGS. 4a, b illustrates the operation of the shield assembly; and,

DETAILED DESCRIPTION OF THE INVENTION

Although the principles of the invention are applicable to other similar types of surgical stapler apparatus, the invention will be understood clearly from an explanation of its application to the surgical stapler apparatus of the type mentioned above. The invention is applicable also to both permanent and disposable apparatus.

Accordingly, although the invention will be illustrated in a disposable embodiment, it could equally be applicable to a disposable cartridge comprising a fastener holder and an anvil assembly mounted in a permanent instrument.

The surgical stapler apparatus of this invention may be of the type similar to those shown in U.S. Pat. Nos. 4,354,628 and 4,665,916. The disclosures of these patents are incorporated by reference herein.

Figure 1:
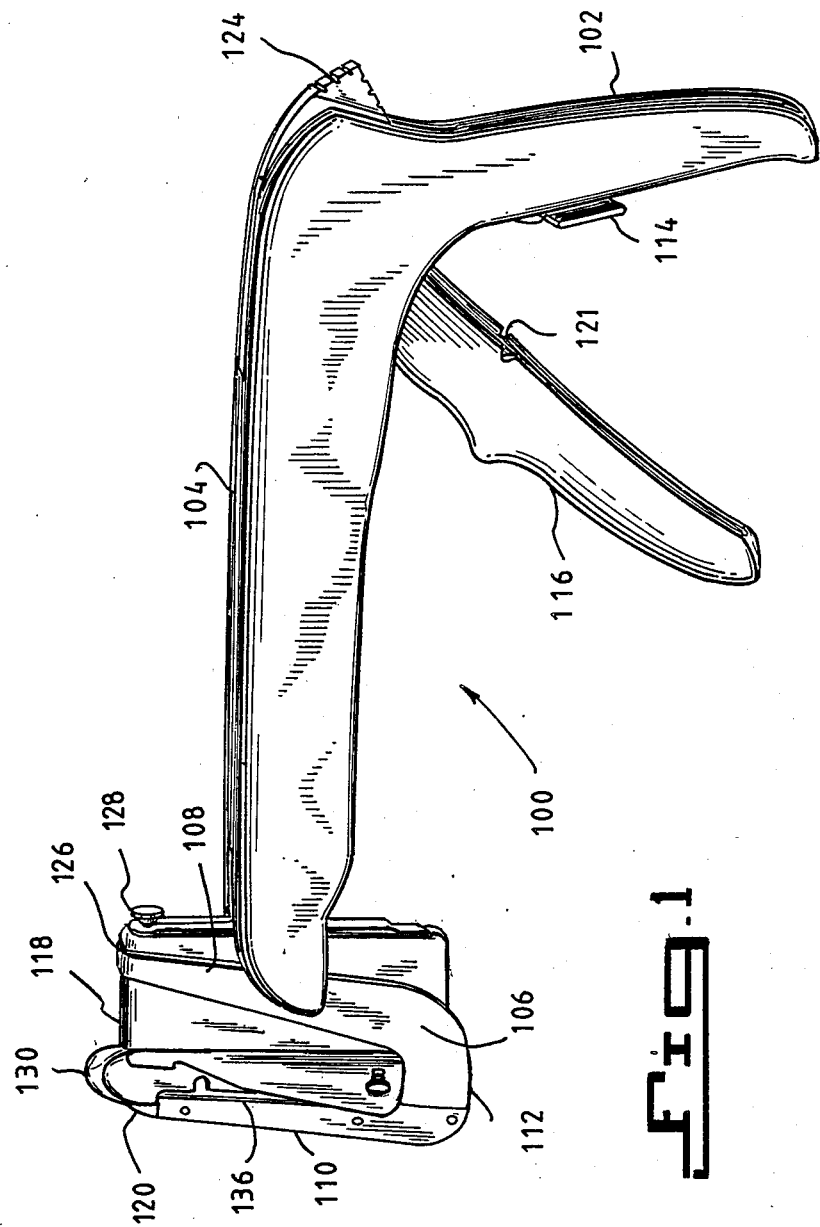
FIG. 1 illustrates the surgical stapler with shield assembly.

As shown in FIG. 1 herein, instrument 100 includes handle 102 adjacent the proximal end of the instrument, a longitudinal connecting structure 104 substantially perpendicular to handle 102, and an open U-shaped support structure 106 at the distal end of connecting structure 104; a means such as actuating lever 124 for positioning the fastener holder 118, a means such as gripping lever 116 for driving the fasteners, and an anvil assembly support housing 120. Said anvil assembly support housing 120 is riveted to the distal leg 110 of the U-shaped distal support 106, and retains and supports anvil assembly 136 which snaps into said anvil assembly support housing 120. The anvil assembly 136 is the holder for the retainer portions 515 (see FIG. 5) of the two part fasteners. The improvement comprises the shield assembly 130 which is attached to the anvil assembly 136. The shield assembly 130 automatically pushes aside extraneous surrounding tissue as the surgeon positions the stapler for the joining operation, and it further adjusts itself to regulate the gap distance between the fastener holder 118 and anvil assembly 136.

Figure 5:
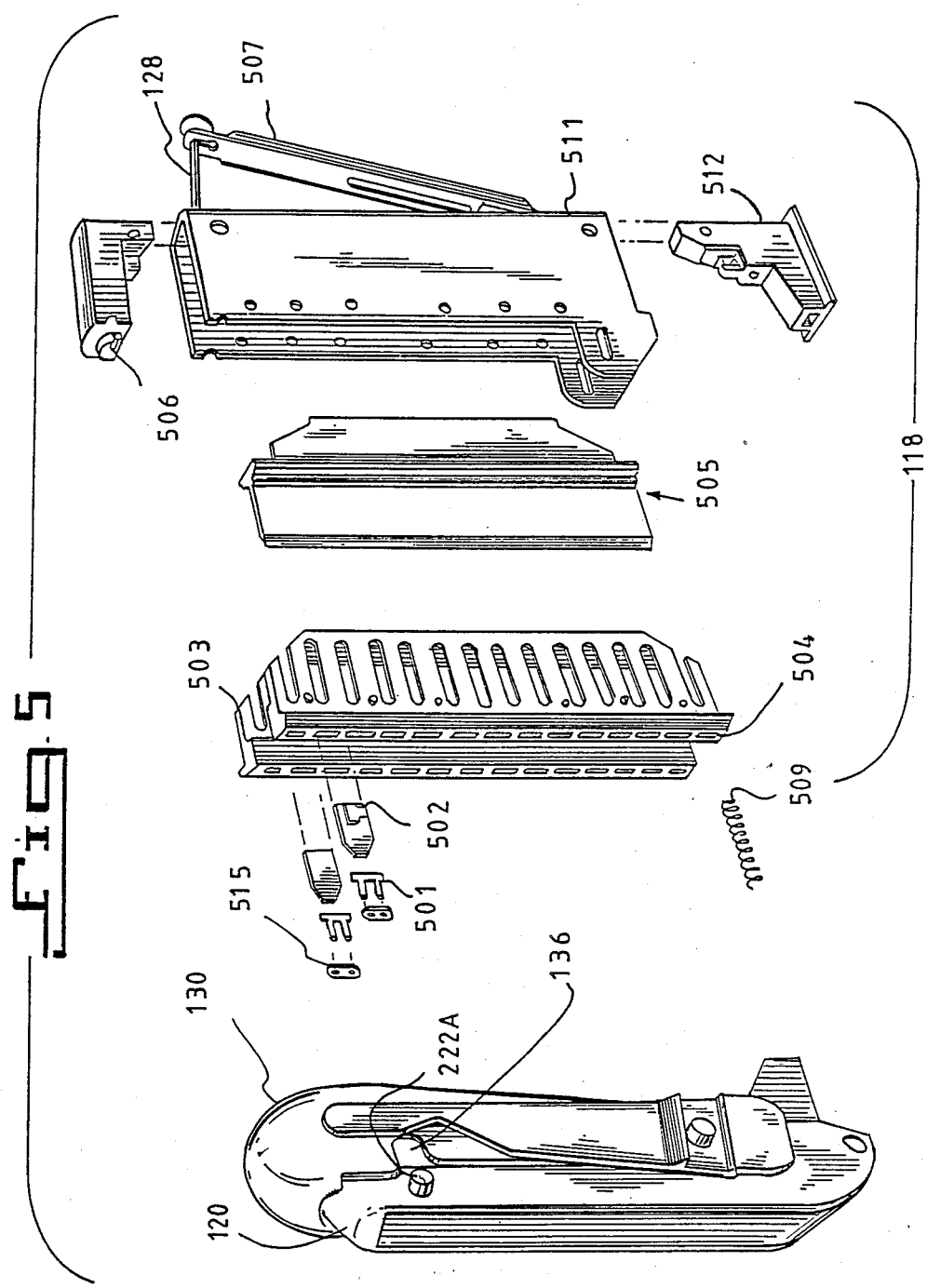
FIG. 5 illustrates an exploded detailed view of the fastener holder.

FIG. 5 shows a detailed exploded view of the interior of the fastener holder 118, which contains fasteners 501, fastener pushers 502, pusher holder 503 with elongated slots 504 for fasteners, knife blade 505, housing 511, spacer 506, alignment pin 128 with spring 507, and base portion 512. As can be seen from FIG. 5, fastener holder 118 is aligned with anvil assembly housing 120 to which it is pivotably connected. This alignment is aided by alignment pin 128 which pierces the target time and is received into depression 303 (see FIG. 2) in the anvil assembly support housing 120. Retainers 515 are held in the anvil assembly 136 and are released upon engagement with fasteners 501 when the surgical staple 100 is actuated. Spring 509, biases the fastener holder toward an open position.

Referring again to FIG. 1, the surgical stapler 100 is operated by positioning it such that body tissue to be joined is in the gap between the fastener holder 118, and the anvil assembly support housing 120, to which the holder 118 is pivotally mounted at the base 112 of the U-shaped distal support 106. The anvil assembly support housing 120 is mounted on the distal leg 110 of the distal support 106. The fastener holder is mounted within the proximal leg 108 of the distal support 106.

When the stapler 100 is properly positioned with respect to the tissue the actuator lever 124 is rotated clockwise, thereby pivoting the fastener holder 118 so that it is aligned against the anvil assembly support housing 120. Alignment pin 128 and arch 126 guide the fastener holder 118 into alignment.

The fastener holder 118 is actuated by rotating the gripping lever 116 counterclockwise to operate the drive assembly for driving the fasteners and optionally a knife blade into the tissue. Safety latch 114 is normally in a raised position wherein it engages notches 121 to prevent the gripping lever 116 from being rotated. To operate the stapler 100, safety latch 114 is rotated downward to the position as shown in FIG. 1.

Shield assembly 130 is mounted on the anvil assembly 136 and extends beyond the edge of the anvil assembly support housing 120.

Figure 2:
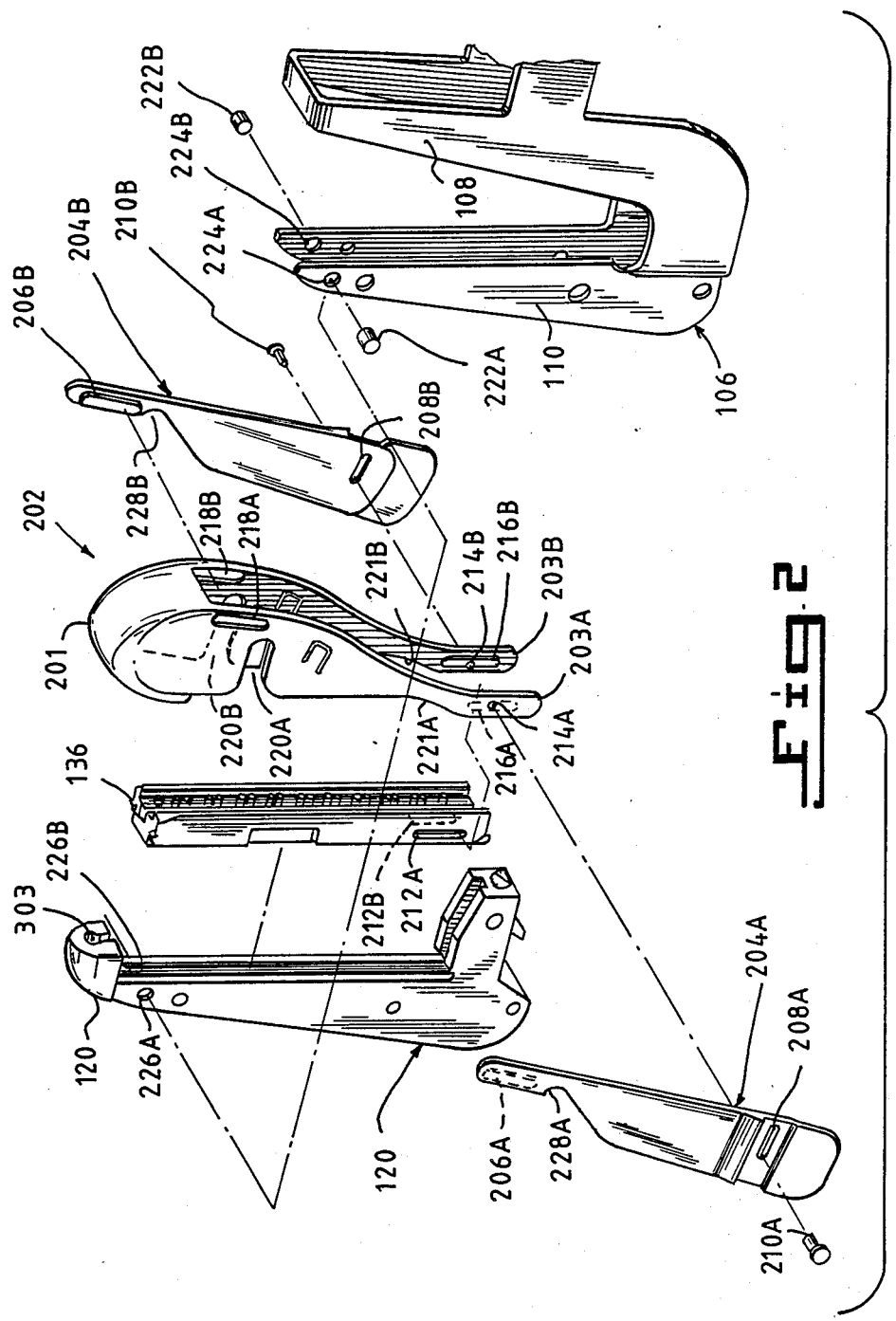
FIG. 2 illustrates an exploded view of the shield assembly.
Figure 3:
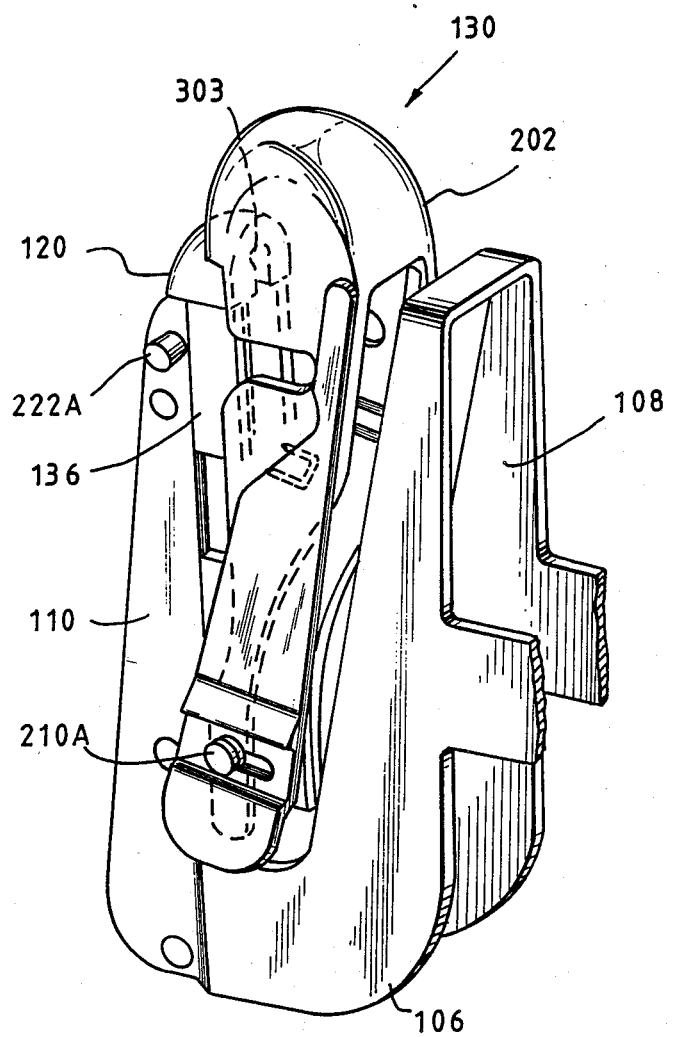
FIG. 3 illustrates the assembled shield assembly in mounted position on the anvil assembly.

As can be seen more clearly in FIGS. 2 and 3, the shield assembly 130 is composed of a flexible wedge 202, and two shutters 204A, and 204B attached to the outer sides of the wedge 202.

Depression 303 in the anvil assembly support housing 120 is for receiving alignment pin 128 when the stapler mechanism is actuated.

The wedge 202 is a substantially U-shaped structure with a rounded end 201 and two prongs 203A and 203B opposite end 201. The inside surfaces of the prongs 203A and 203B each have an elongated detent 216A and 216B respectively and hole 214A and 214B respectively. The detents are engaged by notches 212A and 212B in the anvil assembly 136 and are fixedly mounted therein by adhesive.

Elongated Notches 218A and 218B in the wedge 202 are adapted to engage detents 206A and 206B respectively in the shutters, 204A and 204B which are adhesively fixed therein. The shutter blades 204A and 204B have elongated notches 208A and 208B, respectively. Pivot pins 210A and 210B are disposed respectively through elongated notches 208A and 208B in the shutter blades, and holes 214A and 214B in the wedge member, and are set into the anvil assembly 136.

Indentations 221A and 221B in the distal edges of prongs 203A and 203B and indentations 228A and 228B in the distal edges of shutters 204A and 204B respectively permit the wedge 202 and shutters 204A and 204B to pivot flexibly in a direction distal to the stapler. Stop pins 222A and 222B disposed respectively through holes 224A and 224B in the distal support 106, and into set holes 226A and 226B in the anvil assembly support housing 120, engage indentations 220A and 220B in prongs 203A and 203B thereby limiting the degree to which the wedge 202 pivots in the distal direction. The width of prongs 203A and 203B varies from the fixed end at detents 216A and 216B where the prongs 203A and 203B are no wider than the sides of the anvil assembly 136 to which they are attached, to the rounded end 201 where prongs 203A and 203B are wider than the sides of the anvil assembly 136 thereby extending beyond the surface of the anvil assembly 136 and closing off entry into the gap space between the anvil assembly 136 and the fastener holder 118.

Likewise, flat shutter blades 204A and 204B each have a relatively narrow end which is fixedly mounted onto one of each of the two opposite sides of the wedge member 202 in proximity to the rounded end 201 The flat shutter blades extend parallel to the wedge 202 and have wider ends in the proximity of the fixed ends of prongs 203A and 203B respectively. The proximal edge of each of the shutters 204A and 204B extends beyond the surface of the anvil assembly 136 thereby closing off entry into the gap space between the anvil assembly 136 and fastener holder 118.

Shield assembly 130 is molded from a plastic of relatively high mechanical strength, such as polycarbonate polymeric resin. It must be both flexible and resilient. Indentations 221A and 221B on the edges of the prongs 203A and 203B distal to the stapler 100 facilitate the flexible pivoting of the high strength polymer to a degree sufficient for the shield assembly to perform its function. Likewise, indentations 228A and 228B in the edges of shutter blades 204A and 204B distal to the stapler 100 enable the shutter blades 204A and 204B to flexibly pivot. Because the fixed ends of the shutter blades 204A and 204B are located on the moving end of the wedge 202, and the fixed end of the prongs 203A and 203B of wedge 202 are located in proximity to the unattached free ends of the shutter blades 204A and 204B, said wedge 202 and shutter blades 204A and 204B exhibit pivoting motions in opposite rotational, directions. That is, when the stapler is positioned for operation on body tissue, both the wedge 202 and shutters 204A and 204B will pivot in a direction distal to the stapler 100, but the wedge 202 will pivot in a counterclockwise motion and the shutters 203A and 203B will pivot in clockwise motion.

Shutters 203A and 203B not only exhibit pivoting motion. Since the shutter detents 206A and 206B are mounted at the moving end of the wedge 202, the overall motion of the shutters 203A and 203B is translational as well as rotational. This combined movement insures that the proximal edges of the shutter 204A and 204B which will be contacting the targeted body tissue to be joined by the stapler, will be in parallel alignment with the tissue to form a flush seal, thereby preventing gaps through which extraneous tissue might enter between the anvil assembly and fastener holder.

FIGS. 4A and 4B illustrate the functioning of the invention. In FIG. 4A the distal end of the surgical stapler is being brought into position to join body tissue 402. Extraneous tissue 404 underneath tissue 402 would be unseen by the surgeon. But as the legs of the support structure are brought around the tissue, as can be seen in FIG. 4B, the shield assembly 130 wedges aside the extraneous tissue 404. The end 201 of wedge 202 is rounded so as to facilitate the wedge action of member 202.

The shield assembly 130 is free to flex pivotably between a first proximal position and a second distal position in response to pressure exerted upon it by body tissue 402 as the surgeon positions stapler 100 for operation When targeted tissue 402 enters the gap between the anvil assembly 136 and the fastener holder 118, the shield assembly 130 bends in a direction distal to that of the stapler in response to the pressure exerted upon it. Nevertheless, its resiliency biases it back in a proximal direction towards its unflexed position. The proximal edge of each of the shutters 204A and 204B contacts the tissue 402 and creates a seal thereby closing off space whereby extraneous tissue 404 would otherwise find entry into the gap. Extraneous tissue is therefore deflected and protected from the operation of the stapler.

While the above description contains many specifics, these specifics should not be construed as limitations on the scope of the invention, but merely as exemplifications of preferred embodiments thereof. Those skilled in the art will envision many other possible variations which are within its scope. For example, skilled artisans will readily be able to change the dimensions or use different materials of construction. Therefore, although the invention has been described with reference to certain preferred embodiments, it will be appreciated that other stapler constructions maybe devised, which are nevertheless within the scope and spirit of the invention as defined by the claims appended hereto.

What is claimed is:

1. In an improved surgical stapler for substantially simultaneously applying a plurality of surgical fasteners to body tissue comprising a handle, a gripping lever, a frame with a U-shaped distal portion, an anvil assembly mounted at the distal leg of the U-shaped distal portion, a fastener holder pivotally connected to the anvil assembly adjacent one end of the anvil assembly thereby defining a gap between them and containing a plurality of surgical fasteners and optionally including a knife means for cutting body tissue, the stapler mechanism further including a fastener driving means for substantially simultaneously driving all of the fasteners from the fastener holder, and means for actuating the fastener holder, the improvement comprising:

shield assembly means mounted on the sides of the anvil assembly for preventing extraneous body tissue from being operated upon the surgical stapler, said shield assembly means comprising a wedge member for separating the extraneous tissue from the body tissue to be fastened and two shutter blades acting in cooperation with the wedge member for deflecting the extraneous tissue from entering the gap between the anvil assembly and the fastener holder.

2. The surgical stapler of claim 1 wherein the wedge member is a substantially U-shaped member having a rounded end and two prongs, the inside surfaces of said prongs being fixed at one end to the sides of the anvil assembly, and the rounded end of the wedge extending beyond the anvil assembly.

3. The surgical stapler of claim 2 wherein the shield assembly is flexibly moveable in response to pressure between a first proximal position and a second distal position.

4. The surgical stapler of claim 3 wherein the wedge means and the shutter blades are flexibly pivotable in opposite directions of rotation.

5. The surgical stapler of claim 4 wherein the two prongs of the wedge means each have an indentation on the edge of the prong distal to the stapler to facilitate flexing, and the shutter blades each have an indentation on the edge of the blade distal to the stapler to facilitate flexing.

6. The surgical stapler of claim 3 wherein the shield assembly is resiliently biased to its proximal first position.

7. The invention of claim 2 wherein the two shutter blades each have a relatively narrow end fixedly mounted to one of each of two opposite sides of the wedge member in proximity to the rounded end of said wedge member, and having a relatively wider end in proximity to the fixed end of the prongs of the wedge member.

8. The surgical stapler of claim 1 wherein the shield assembly is made of resilient material.

9. The surgical stapler of claim 7 wherein the resilient material is a polymeric material.

10. The surgical stapler of claim 8 wherein the polymeric material is a polycarbonate.

11. In an improved surgical stapler for substantially simultaneously applying a plurality of surgical fasteners to body tissue comprising a handle, a gripping lever, a frame with a U-shaped distal portion, an anvil assembly mounted at the distal leg of the U-shaped distal portion, a fastener holder pivotally connected to the anvil assembly adjacent one end of the anvil assembly thereby defining a gap between them and containing a plurality of surgical fasteners and including a knife means for cutting body tissue, the stapler mechanism further including a fastener driving means for substantially simultaneously driving all of the fasteners from the fastener holder, and means for actuating the fastener holder, the improvement comprising:

shield assembly means mounted on the sides of the anvil assembly for preventing extraneous body tissue from being operated upon the surgical stapler, said shield assembly means comprising a wedge member for separating the extraneous tissue from the body tissue to be fastened and two shutter blades acting in cooperation with the wedge member for deflecting the extraneous tissue from entering the gap between the anvil assembly and the fastener holder.

12. The surgical stapler of claim 11 wherein the wedge member is a substantially U-shaped member having a rounded end and two prongs, the inside surfaces of said prongs being fixed at one end to the sides of the anvil assembly, and the rounded end of the wedge extending beyond the anvil assembly.

13. The surgical stapler of claim 12 wherein the shield assembly is flexibly moveable in response to pressure between a first proximal position and a second distal position.

14. The surgical stapler of claim 13 wherein the wedge means and the shutter blades are flexibly pivotable in opposite directions of rotation.

15. The surgical stapler of claim 14 wherein the two prongs of the wedge means each have an indentation on the edge of the prong distal to the stapler to facilitate flexing, and the shutter blades each have an indentation on the edge of the blade distal to the stapler to facilitate flexing.

16. The surgical stapler of claim 13 wherein the shield assembly is resiliently biased to its proximal first position.

17. The surgical stapler of claim 11 wherein the shield assembly is made of resilient material.

18. The surgical stapler of claim 17 wherein the resilient material is a polymeric material.

19. The surgical stapler of claim 18 wherein the polymeric material is a polycarbonate.

20. The invention of claim 11 wherein the two shutter blades each have a relatively narrow end fixedly mounted to one of each of two opposite sides of the wedge member in proximity to the rounded end of said wedge member, and having a relatively wider end in proximity to the fixed end of the prongs of the wedge member.

* * * * *